(12) United States Patent
Carlson et al.

(10) Patent No.: US 12,121,739 B2
(45) Date of Patent: Oct. 22, 2024

(54) METHODS, SYSTEMS, AND APPARATUSES FOR MANAGING TEMPERATURES INDUCED BY ALTERNATING FIELDS

(71) Applicant: Novocure GmbH, Root D4 (CH)

(72) Inventors: Kristen W. Carlson, Concord, MA (US); Zeev Bomzon, Haifa (IL)

(73) Assignee: Novocure GmbH, Root (CH)

( * ) Notice: Subject to any disclaimer, the term of this patent is extended or adjusted under 35 U.S.C. 154(b) by 0 days.

(21) Appl. No.: 17/118,056

(22) Filed: Dec. 10, 2020

(65) Prior Publication Data

US 2021/0196967 A1  Jul. 1, 2021

Related U.S. Application Data

(60) Provisional application No. 62/955,747, filed on Dec. 31, 2019.

(51) Int. Cl.
*A61N 1/40* (2006.01)
*A61N 1/04* (2006.01)

(52) U.S. Cl.
CPC ............ *A61N 1/40* (2013.01); *A61N 1/0476* (2013.01)

(58) Field of Classification Search
None
See application file for complete search history.

(56) References Cited

U.S. PATENT DOCUMENTS

| | | | |
|---|---|---|---|
| 4,228,809 A * | 10/1980 | Paglione | G05D 23/1909 219/718 |
| 4,676,258 A | 6/1987 | Inokuchi et al. | |
| 5,081,988 A | 1/1992 | Cook et al. | |
| 5,873,849 A | 2/1999 | Bernard | |
| 5,938,597 A | 8/1999 | Stratbucker | |
| 5,974,344 A | 10/1999 | Shoemaker, II | |
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |

(Continued)

FOREIGN PATENT DOCUMENTS

| | | |
|---|---|---|
| CN | 107281635 A | 10/2017 |
| CN | 305338240 S | 9/2019 |

(Continued)

OTHER PUBLICATIONS

Bomzon et al., "Using Computational Phantoms to Improve the Delivery of Tumor Treating Fields (TTFields) to Patients," 38th Annual International Conference of the IEEE Engineering in Medicine and Biology Society (EMBC), IEEE, pp. 6461-6464, 2016.

(Continued)

*Primary Examiner* — Michael W Kahelin

(74) *Attorney, Agent, or Firm* — McCarter & English, LLP; Michael A. Sartori

(57) ABSTRACT

Methods, systems, and apparatuses are described for managing temperatures induces my alternating electric fields by selectively activating/deactivating electrodes of a pair of transducer arrays according to defined parameters.

9 Claims, 12 Drawing Sheets

(56) References Cited

U.S. PATENT DOCUMENTS

| | | |
|---|---|---|
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,910,453 B2 | 3/2018 | Wasserman et al. |
| 10,188,851 B2 | 1/2019 | Wenger et al. |
| 10,265,530 B1 | 4/2019 | Perryman et al. |
| 10,441,776 B2 | 10/2019 | Kirson et al. |
| 10,675,460 B2 | 6/2020 | Travers et al. |
| 10,779,875 B2 | 9/2020 | Palti et al. |
| 10,821,283 B2 | 11/2020 | Giladi et al. |
| 2004/0122500 A1 | 6/2004 | Rouns |
| 2005/0222646 A1 | 10/2005 | Kroll et al. |
| 2006/0149341 A1* | 7/2006 | Palti .............. A61N 1/0492 600/372 |
| 2006/0167499 A1 | 7/2006 | Palti |
| 2007/0043405 A1* | 2/2007 | Rittman, III ....... A61N 1/36021 607/72 |
| 2007/0093788 A1 | 4/2007 | Carter |
| 2007/0225766 A1* | 9/2007 | Palti .............. A61N 1/36002 607/2 |
| 2008/0183251 A1 | 7/2008 | Azar et al. |
| 2008/0319372 A1 | 12/2008 | Palti et al. |
| 2010/0204560 A1 | 8/2010 | Salahieh et al. |
| 2012/0029500 A1 | 2/2012 | Jenson |
| 2014/0005759 A1* | 1/2014 | Fahey ............... A61N 1/0476 607/114 |
| 2015/0112328 A1 | 4/2015 | Williard et al. |
| 2015/0320481 A1 | 11/2015 | Cosman, Jr. et al. |
| 2016/0022986 A1* | 1/2016 | Travers ............ A61N 1/36002 607/148 |
| 2016/0346530 A1 | 12/2016 | Jeffery et al. |
| 2017/0014637 A1 | 1/2017 | Basser |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0085575 A1 | 3/2018 | Travers et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1* | 4/2019 | Travers .............. A61N 1/37217 |
| 2019/0223946 A1 | 7/2019 | Coates et al. |
| 2019/0307781 A1 | 10/2019 | Krex et al. |
| 2019/0308016 A1 | 10/2019 | Wenger et al. |
| 2019/0314631 A1 | 10/2019 | Wong et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2021/0038892 A1* | 2/2021 | Velasco Valcke ..... A61N 2/002 |

FOREIGN PATENT DOCUMENTS

| | | |
|---|---|---|
| JP | 2008-532564 A | 8/2008 |
| JP | 2009-520509 A | 5/2009 |
| JP | 2009-544399 A | 12/2009 |
| JP | 2010-536406 A | 12/2010 |
| JP | 2019-524206 A | 9/2019 |
| WO | 02/047565 A2 | 6/2002 |
| WO | 03/002185 A2 | 1/2003 |
| WO | WO-2009/022225 A1 | 2/2009 |
| WO | 2014/025394 A1 | 2/2014 |
| WO | 2016/014264 A1 | 1/2016 |
| WO | 2017/141257 A1 | 8/2017 |
| WO | WO-2019/155407 A2 | 8/2019 |

OTHER PUBLICATIONS

Korshoej et al., "Enhancing Predicted Efficacy of Tumor Treating Fields Therapy of Glioblastoma Using Targeted Surgical Craniectomy: A Computer Modeling Study," PLOS ONE, vol. 11, No. 10, p. e0164051, Oct. 2016.

Miranda et al., "Predicting the electric field distribution in the brain for the treatment of glioblastoma," Physics in Medicine & Biology, vol. 50, pp. 4137-4147, Jul. 2014.

Ballo et al, "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial," Int J Radiation Oncol Biol Phys, vol. 104, No. 5, 2019, pp. 1106-1113.

Extended European Search Report issued in EP Application No. 22177338.5, mailed Sep. 14, 2022.

* cited by examiner

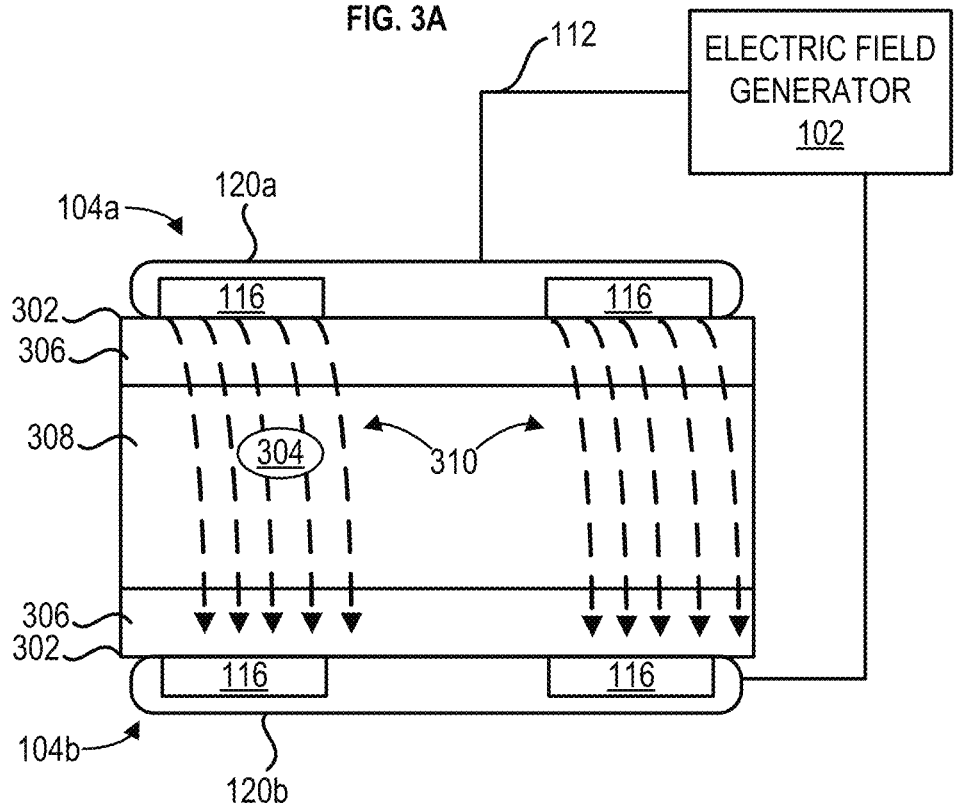
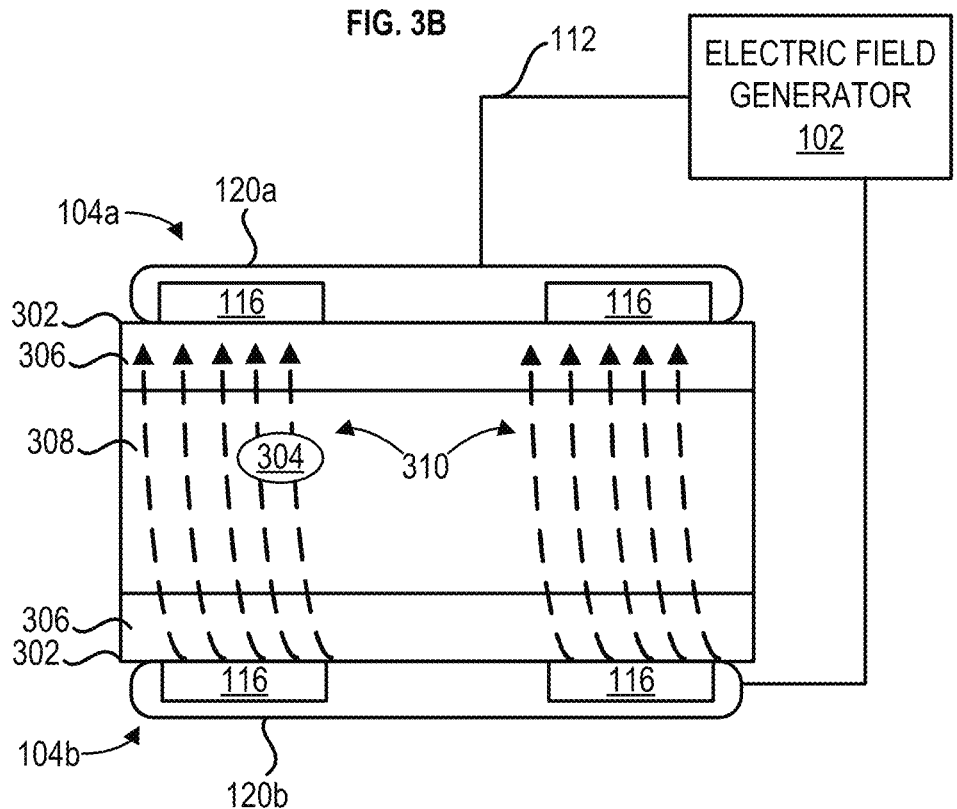

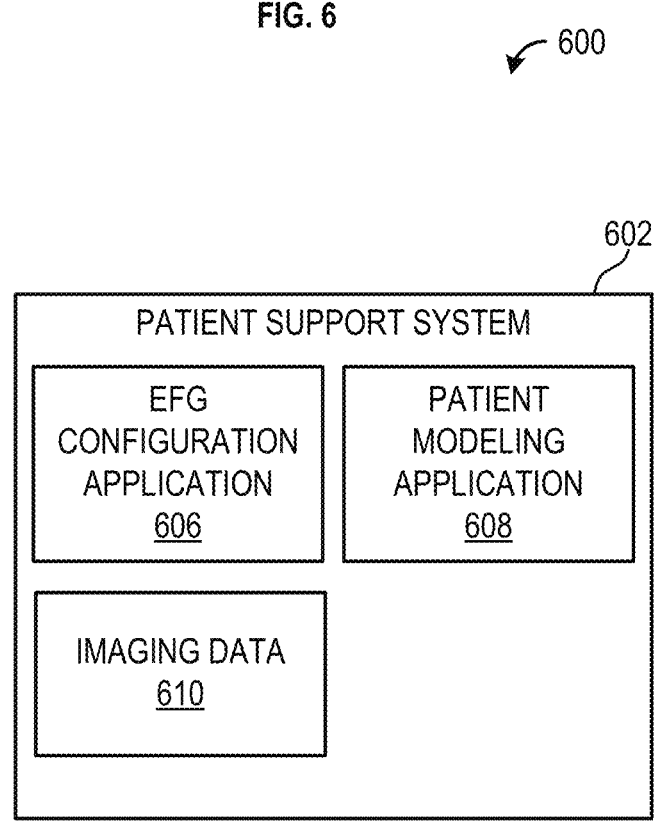

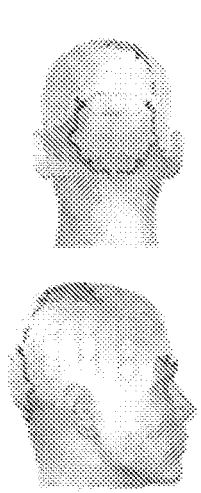
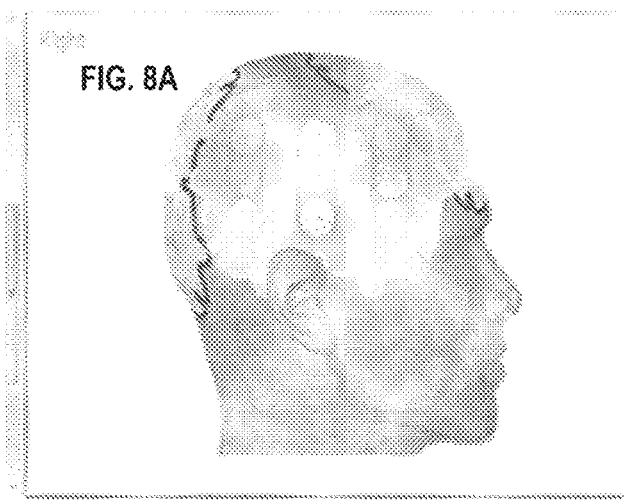
FIG. 8A
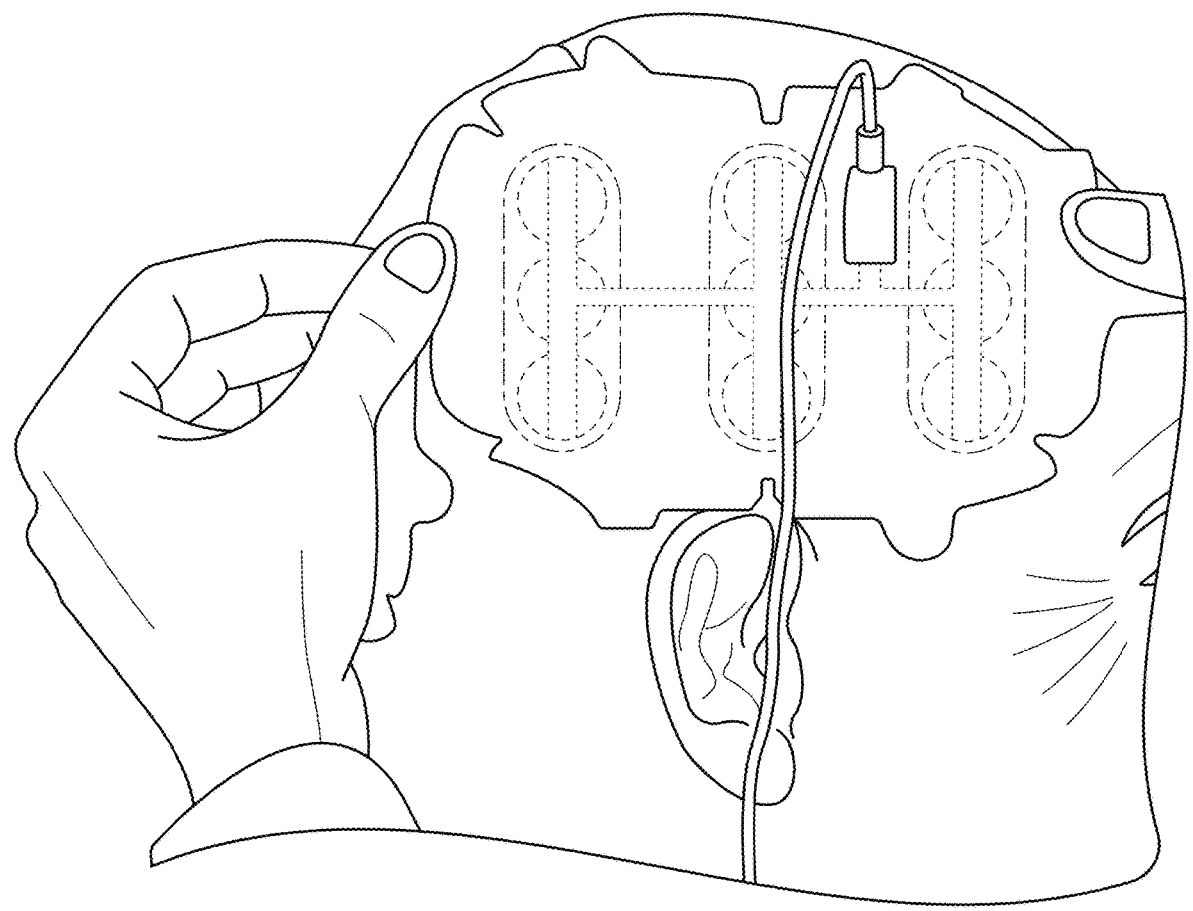
FIG. 8B

CAUSING CYCLICAL APPLICATION OF A FIRST ELECTRIC FIELD IN A FIRST DIRECTION VIA A FIRST TRANSDUCER ARRAY AND A SECOND ELECTRIC FIELD IN A SECOND DIRECTION, OPPOSITE THE FIRST DIRECTION, VIA A SECOND TRANSDUCER ARRAY

1120

DURING THE CYCLICAL APPLICATION: DEACTIVATING ONE OR MORE ELECTRODES OF THE FIRST OR SECOND TRANSDUCER ARRAY BASED ON A TEMPERATURE OF THE ONE OR MORE ELECTRODES SATISFYING A THRESHOLD, AND ACTIVATING THE ONE OR MORE ELECTRODES OF THE FIRST OR SECOND TRANSDUCER ARRAY WHEN THE TEMPERATURE DOES NOT SATISFY THE THRESHOLD

1210
CAUSING CYCLICAL APPLICATION OF A FIRST ELECTRIC FIELD IN A FIRST DIRECTION VIA A FIRST TRANSDUCER ARRAY AND A SECOND ELECTRIC FIELD IN A SECOND DIRECTION TO A REGION OF INTEREST (ROI), OPPOSITE THE FIRST DIRECTION, VIA A SECOND TRANSDUCER ARRAY

1220
DURING THE CYCLICAL APPLICATION: SELECTIVELY DEACTIVATING ONE OR MORE ELECTRODES OF THE FIRST OR SECOND TRANSDUCER ARRAY TO ADJUST AN ANGLE OF THE FIRST OR SECOND ELECTRIC FIELD APPLIED TO THE ROI

METHODS, SYSTEMS, AND APPARATUSES FOR MANAGING TEMPERATURES INDUCED BY ALTERNATING FIELDS

CROSS-REFERENCE TO RELATED PATENT APPLICATION

This application claims priority to U.S. Provisional Application No. 62/955,747 filed Dec. 31, 2019, which is herein incorporated by reference in its entirety.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma and approved combination therapy with chemotherapy for newly diagnosed patients. These electric fields are induced non-invasively by transducer arrays (e.g., arrays of electrodes) placed directly on the patient's scalp. TTFields also appear to be beneficial for treating tumors in other parts of the body. Disparities in tissue types and geometries may reduce the efficacy of alternating electric fields when applied to a target region. Also, the alternating electric fields applied by transducer arrays may produce heat. The heat generated by electrodes of a transducer array may cause patient discomfort at a tissue-transducer interface, such as on the surface of the skin.

SUMMARY

Described are methods comprising causing cyclical application of a first electric field via a first transducer array in a first direction and a second electric field via a second transducer array in a second direction, opposite the first direction, wherein the first transducer array comprises a first plurality of electrodes and the second transducer array comprises a second plurality of electrodes, and during the cyclical application, deactivating, based on a temperature associated with the one or more electrodes of the first plurality of electrodes or one or more electrodes of the second plurality of electrodes satisfying a threshold, the one or more electrodes of the first plurality of electrodes or the one or more electrodes of the second plurality of electrodes, and activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes.

Also described are methods comprising causing cyclical application of a first electric field via a first transducer array in a first direction and a second electric field via a second transducer array in a second direction, opposite the first direction, to a region of interest, wherein the first transducer array comprises a first plurality of electrodes and the second transducer array comprises a second plurality of electrodes, and during the cyclical application, selectively deactivating, one or more electrodes of the first plurality of electrodes or one or more electrodes of the second plurality of electrodes, to adjust an angle at which the first electric field or the second electric field is applied to the region of interest.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 3A and FIG. 3B illustrate an example application of the apparatus for electrotherapeutic treatment.

FIG. 6 is a block diagram depicting an electric field generator and a patient support system.

FIG. 8A shows a three-dimensional array layout map 800.

FIG. 8B shows the placement of transducer arrays on the scalp of a patient.

FIG. 11 shows an example method.

FIG. 12 shows an example method.

DETAILED DESCRIPTION

Figure 1:
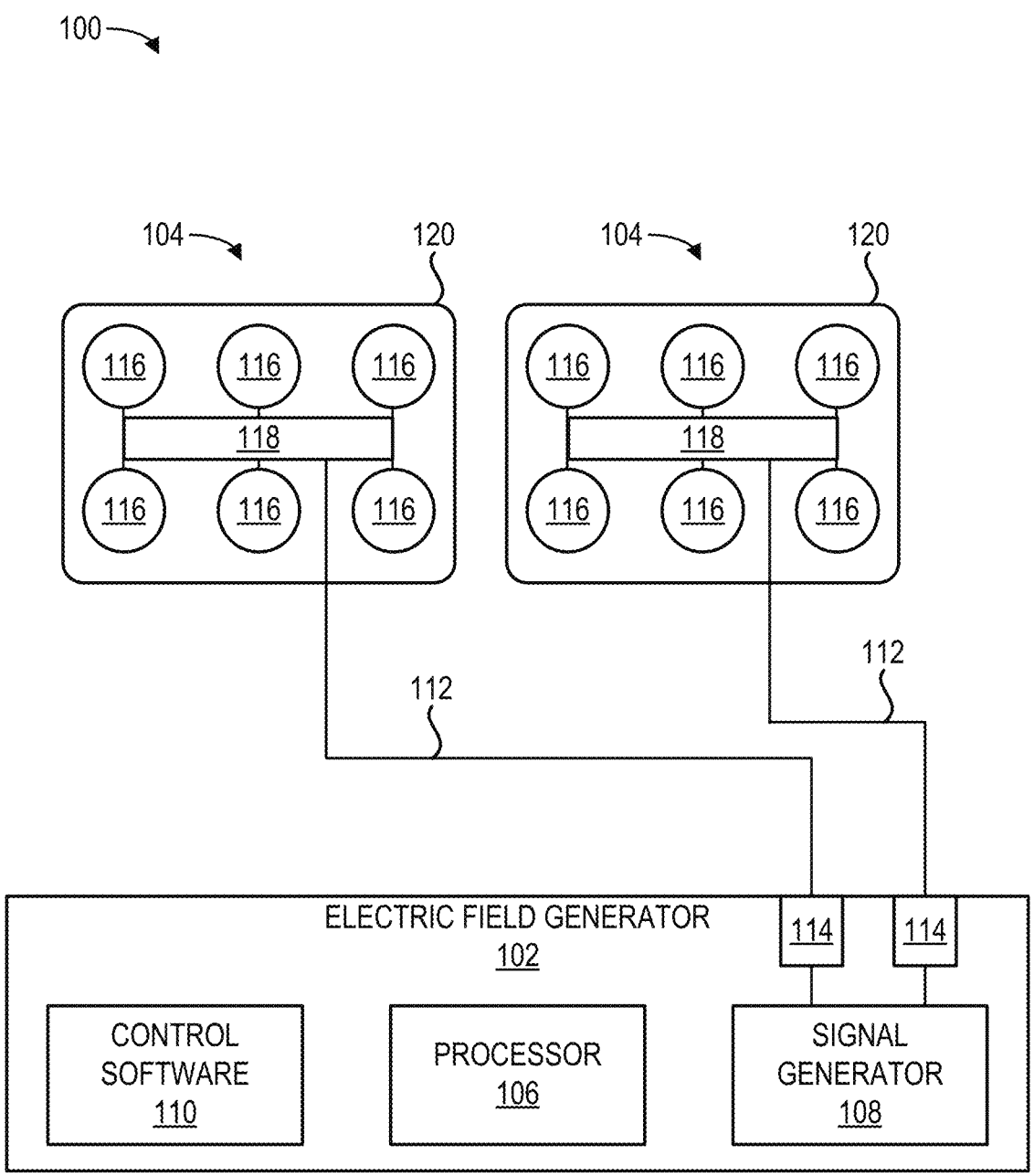
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electric fields, are established as an anti-mitotic cancer treatment modality because they interfere with proper microtubule assembly during metaphase and eventually destroy the cells during telophase and cytokinesis. The efficacy increases with increasing field strength and the optimal frequency are cancer cell line dependent with 200 kHz being the frequency for which inhibition of glioma cell growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (e.g., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electric fields and then another pair of the three transducer arrays may deliver the alternating electric fields, and the remaining pair of the three transducer arrays may deliver the alternating electric fields.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electric field distributes within the head as a function of the positions of the array and, in some aspects, take account for variations in the electrical property distributions within the heads of different patients.

FIG. 1 shows an example apparatus 100 for electrotherapeutic treatment. Generally, the apparatus 100 may be a portable, battery or power supply operated device which produces alternating electric fields within the body by means of non-invasive surface transducer arrays. The apparatus 100 may comprise an electric field generator 102 and one or more transducer arrays 104. The apparatus 100 may be configured to generate tumor treatment fields (TTFields) (e.g., at 150 kHz) via the electric field generator 102 and deliver the TTFields to an area of the body through the one or more transducer arrays 104. The electric field generator 102 may be a battery and/or power supply operated device. In an embodiment, the one or more transducer arrays 104 are uniformly shaped. In an embodiment, the one or more transducer arrays 104 are not uniformly shaped.

The electric field generator 102 may comprise a processor 106 in communication with a signal generator 108. The electric field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 kHz to about 500 kHz (preferably from about 100 kHz to about 300 kHz) (e.g., the TTFields). The voltages are such that the electric field intensity in tissue to be treated is in the range of about 0.1 V/cm to about 10 V/cm.

One or more outputs 114 of the electric field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and can grounded to prevent the spread of the electric field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal to the signal generator 108 that causes the signal generator 108 to output the desired treatment frequency to the one or more transducer arrays 104.

The one or more transducer arrays 104 may be configured in a variety of shapes and positions to generate an electric field of the desired configuration, direction, and intensity at a target volume to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more thermistors (not shown), for example, 8 thermistors, (accuracy±1° C.). to measure skin temperature beneath the transducer arrays 104. The thermistors may be configured to measure skin temperature periodically, for example, every second. The thermistors may be read by the control software 110 while the TTFields are not being delivered to avoid any interference with the temperature measurements.

If the temperature measured is below a pre-set maximum temperature (Tmax), for example, 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
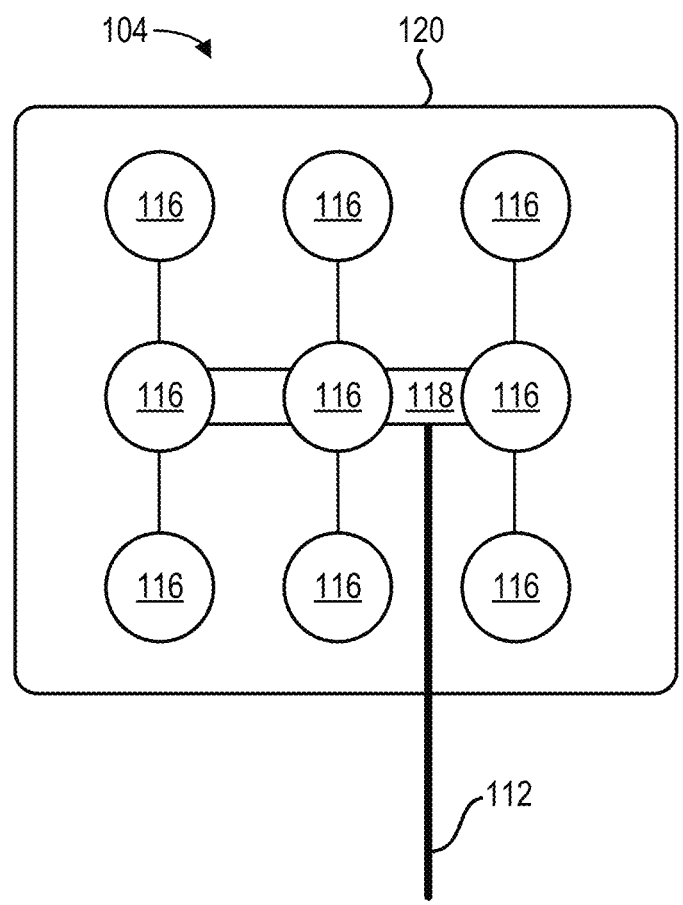
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

Alternative constructions for the one or more transducer arrays 104 are contemplated and may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a subject/patient's body, with no insulating dielectric layer disposed between the conductive elements and the body. Other alternative constructions for implementing the transducer arrays may also be used. Any transducer array (or similar device/component) configuration, arrangement, type, and/or the like may be used for the methods and systems described herein as long as the transducer array (or similar device/component) configuration, arrangement, type, and/or the like is (a) capable of delivering TTFields to a subject/patient's body and (b) and may be positioned arranged, and/or placed on a portion of a patient/subject's body as described herein.

Status of the apparatus 100 and monitored parameters may be stored a memory (not shown) and can be transferred to a computing device over a wired or wireless connection. The apparatus 100 may comprise a display (not shown) for displaying visual indicators, such as, power on, treatment on, alarms, and low battery.

FIG. 3A and FIG. 3B illustrate an example application of the apparatus 100. A transducer array 104a and a transducer array 104b are shown, each incorporated into a hypoallergenic medical adhesive bandage 120a and 120b, respectively. The hypoallergenic medical adhesive bandages 120a and 120b are applied to skin surface 302. A tumor 304 is located below the skin surface 302 and bone tissue 306 and is located within brain tissue 308. The electric field generator 102 causes the transducer array 104a and the transducer array 104b to generate alternating electric fields 310 within the brain tissue 308 that disrupt rapid cell division exhibited by cancer cells of the tumor 304. The alternating electric fields 310 have been shown in non-clinical experiments to arrest the proliferation of tumor cells and/or to destroy them. Use of the alternating electric fields 310 takes advantage of the special characteristics, geometrical shape, and rate of dividing cancer cells, which make them susceptible to the effects of the alternating electric fields 310. The alternating electric fields 310 alter their polarity at an intermediate frequency (on the order of 100-300 kHz). The frequency used for a particular treatment may be specific to the cell type being treated (e.g., 150 kHz for MPM). The alternating electric fields 310 have been shown to disrupt mitotic spindle microtubule assembly and to lead to dielectrophoretic dislocation of intracellular macromolecules and organelles during cytokinesis. These processes lead to the physical disruption of the cell membrane and programmed cell death (apoptosis).

Because the effect of the alternating electric fields 310 is directional with cells dividing parallel to the field affected more than cells dividing in other directions, and because cells divide in all directions, alternating electric fields 310 may be delivered through two pairs of transducer arrays 104 that generate perpendicular fields within the treated tumor. Theory and modeling predict that the directional, tumor-killing effect of the alternating electric fields 310 is due to their disruption of cellular structures whose spatial orientation renders them maximally susceptible to the disruptive effect when they are parallel to the alternating electric fields 310. Thus, theory and modeling predict that changing the direction of the alternating electric fields 310 multiple times in specific directions will have the maximal disruptive effect on the cellular structures, with each added change of direction reducing the variance of electric field strength received by the cellular structure. Thus, if the mean field strength at the cell is what is required to kill the cell if all cellular structures were aligned with the field (e.g., 'efficacious' field strength), without changing the field direction, some structures see less than efficacious field strength while some see more than efficacious field strength, while with changes of direction, fewer structures see sub-efficacious field strength with the harmless trade-off that fewer structures at supra-efficacious see reduced field strength that is still supra-efficacious. More specifically, one pair of transducer arrays 104 may be located to the left and right (LR) of the tumor, and the other pair of transducer arrays 104 may be located anterior and posterior (AP) to the tumor. Cycling the alternating electric fields 310 between these two directions (e.g., LR and AP) ensures that a larger range of cell orientations is targeted than with one direction only. In an embodiment, the alternating electric fields 310 may be delivered according to a symmetric setup of transducer arrays 104 (e.g., four total transducer arrays 104, two matched pairs). In another embodiment, the alternating electric fields 310 may be delivered according to an asymmetric setup of transducer arrays 104 (e.g., three total transducer arrays 104). An asymmetric setup of transducer arrays 104 may engage two of the three transducer arrays 104 to deliver the alternating electric fields 310 and then switch to another two of the three transducer arrays 104 to deliver the alternating electric fields 310, and the like. In an embodiment, subsets of transducer arrays 104 may be used to achieve more changes of direction of the alternating electric fields 310 than are possible by using the full transducer array 104 in each location.

In other embodiments, the changes of direction of electric fields 310 via transducer arrays, or their subset transducers, would attempt to attain the following angles for each number of directions: 90 degrees in two dimensions for two directions, 90 degrees in three directions, all orthogonal to each other, in three dimensions, and the dihedral angle of the tetrahedron (70.53 degrees) in three dimensions with four changes.

Electric fields (e.g., the alternating electric fields 310, etc.) may heat tissue (e.g., the skin surface 302, etc.) under and/or near transducers. Also, because different regions of a patient's body are composed of different geometric shapes and electrical properties, the conductivity of tissues may vary according to orientation to an imposed field causing inhomogeneous concentrations of field strength. Further, an electric field may be reduced in strength and efficacy (e.g., shunted, etc.) due to the presence of conductive body fluids such as cerebrospinal fluid (CSF). In some instances, the apparatus 100 may be configured to reduce and/or eliminate instances of tissue heating at the transducer-tissue interface. For example, the apparatus 100 may be configured to cyclically activate and deactivate electrodes of a transducer array to alter the direction and/or duration of an electric field (e.g., to impose alignment or orthogonality with cell axes within a region-or interest (ROI)) and reduce high-temperature points at the transducer-skin interface by allowing deactivated electrodes to cool to the desired temperature, such as a threshold temperature. An optimal interval at which to alter field direction may be determined by analysis of a tissue model that includes tissue/information from a plurality of patients. Optimal parameters for field strength, frequency, and duration may be determined according to variations in the geometry of various tissue samples the electric field generator 102 may be configured to 'sweep' through various parameter ranges and determine the effect of the parameters on an efficacious dose at a target ROI (e.g., tumor, etc.). When a specific tissue geometry of a patient is unknown and/or tissue geometry is significantly inhomogeneous due to geometry and tissue properties, a random selection of angles at optimal duty cycles determined by the electric field generator 102, such as a 50 ms duty cycle and/or a or temperature-limited duty cycle, may optimize the average therapeutic dose delivered to a target ROI (e.g., tumor, etc.). When a tumor location and/or tissue inhomogeneity of a patient is determined, the electric field generator 102 may activate/deactivate cathode and anode combinations of the transducer arrays 104 based on the location/ placement of the transducer arrays 104 and relative orientation to the geometric center of the target ROI.

In some instances, the apparatus 100 may include one or more thermistors that indicate the temperature state of the one or more electrodes 116 of the transducer arrays 104. A feedback loop may be established between the one or more thermistors and the processor 106 and/or the control software 110. The electric field generator 102, based on the feedback loop, may be configured to optimally maximize current and/or voltage delivered to the transducer arrays 104 by cycling patterns of electric field amplitude changes at fixed or variable cycle lengths. For example, the electric field generator 102 may cyclically and simultaneously deactivate (e.g., turn off amplitude, etc.) one or more electrodes of the transducer arrays 104 with the highest sensed temperatures and activate (e.g., turn on amplitude, etc.) one or more electrodes of the transducer arrays 104 according to a function of electrode temperature and an available selection of angles between electrodes of the transducer arrays 104. In some instances, the function of electrode temperature and inter-electrode angle may be a weighted product of temperature multiplied by a function of the angle between the difference in temperature between two electrodes and an angle between lines drawn from centers of the two electrodes to the geometric center of a target ROI. In some instances, electrodes of the transducer arrays 104 may be activated for durations of decreasing increments such that the temperature of the activated electrodes approaches an asymptotic limit. The decreasing increments of the durations may be based on a difference between the asymptotic limit and the temperature of the activated electrodes at a given point in time.

In some instances, electrodes of the transducer arrays 104 may be activated for durations that are limited by the temperature of the electrodes approaching an asymptotic limit according to the following function:

$$\text{Temp}(t) = \text{Temp}(t-1) * \text{Temp}_{Max} - \text{Exp}[-\text{Temp}(t-1)/\text{Temp}_{max}]), \quad \text{Function 1:}$$

where $\text{Temp}_{Max}$ is a temperature limit set for a transducer region and t is time.

In some instances, electrodes of the transducer arrays 104 may be activated for durations that are limited by the temperature of the electrodes approaching an asymptotic limit according to the following function:

$$\text{Temp}(t) = \text{Temp}(t-1) * \text{Temp}_{Max} - \text{Exp}[-\text{Temp}(t/\tau_{tissue})]), \quad \text{Function 2:}$$

where $\text{Temp}_{Max}$ is a temperature limit set for a transducer region, t is time, and $\tau_{tissue}$ is a time constant for a tissue based on empirical or theoretical estimates of its heat diffusion rate.

In-vivo and in-vitro studies show that the efficacy of TTFields therapy increases as the intensity of the electric field increases. The methods, systems, and apparatuses described are configured for optimizing array placement on the patient's scalp to increase the intensity in the diseased region of the brain.

Figure 4A:
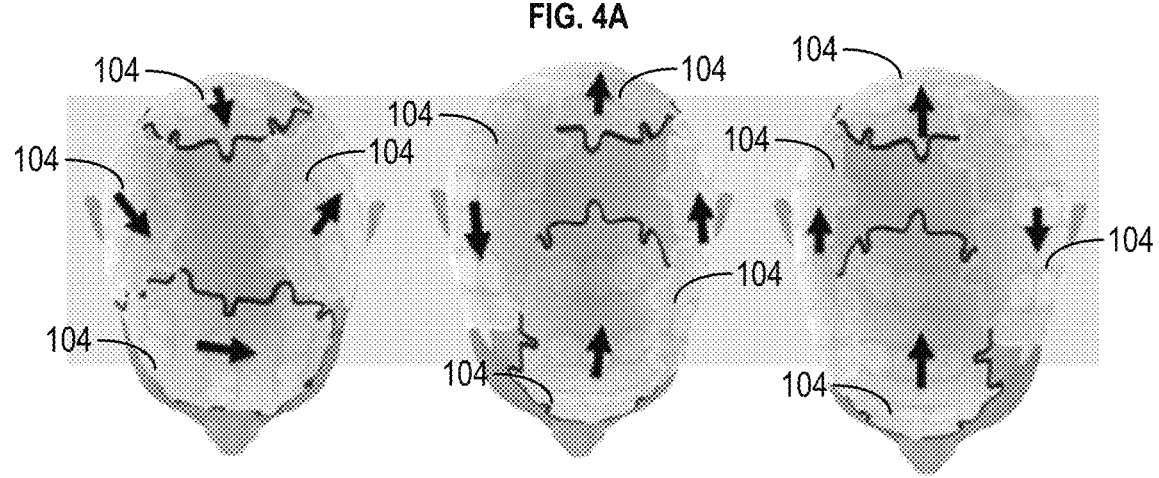
FIG. 4A shows transducer arrays placed on a patient's head.
Figure 4B:
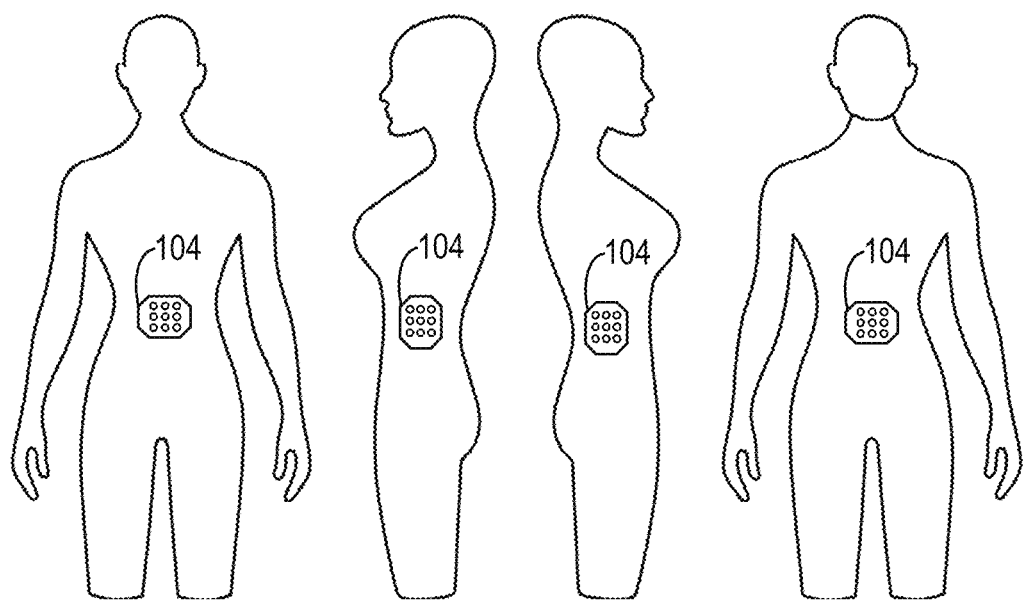
FIG. 4B shows transducer arrays placed on a patient's abdomen.
Figure 5A:
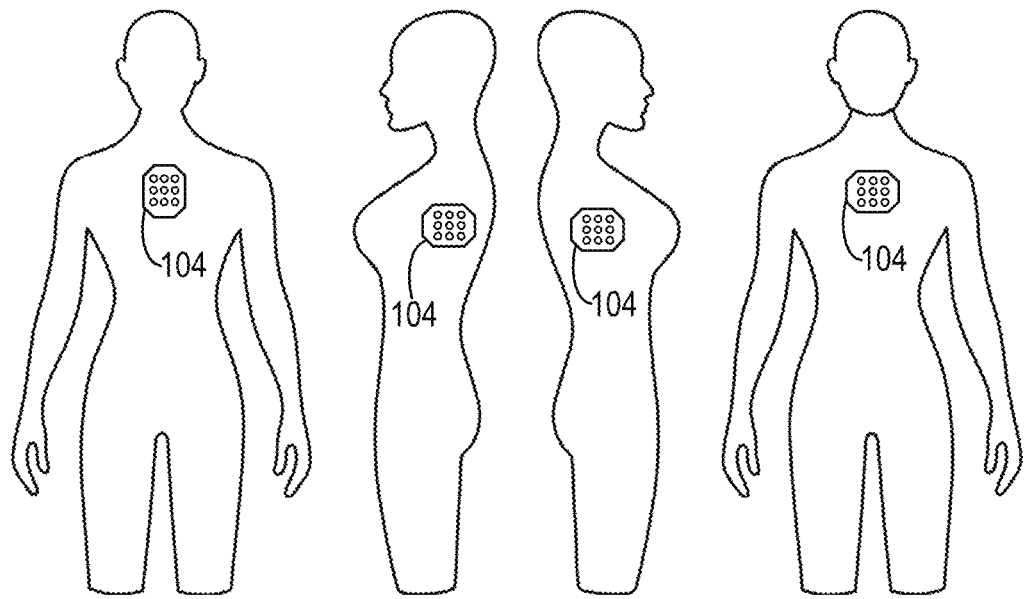
FIG. 5A shows the transducer arrays placed on a patient's torso.
Figure 5B:
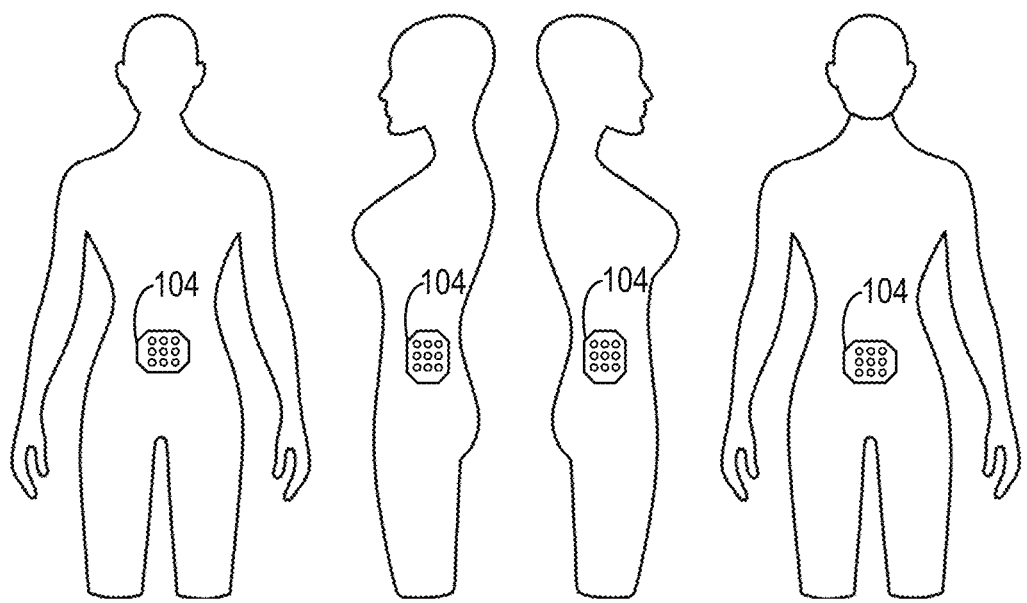
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) are specifically contemplated.

FIG. 6 is a block diagram depicting non-limiting examples of a system 600 comprising a patient support system 602. The patient support system 602 can comprise one or multiple computers configured to operate and/or store an electric field generator (EFG) configuration application 606, a patient modeling application 608, and/or imaging data 610. The patient support system 602 can comprise, for example, a computing device. The patient support system 602 can comprise, for example, a laptop computer, a desktop computer, a mobile phone (e.g., a smartphone), a tablet, and the like.

The patient modeling application 608 may be configured to generate a three dimensional model of a portion of a body of a patient (e.g., a patient model) according to the imaging data 610. The imaging data 610 may comprise any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electric field simulations.

Figure 7:
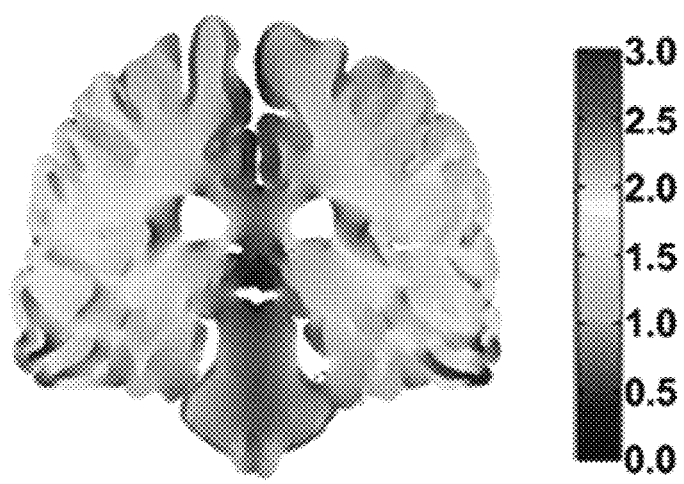
FIG. 7 illustrates electric field magnitude and distribution (in V/cm) shown in the coronal view from a finite element method simulation model.

To properly optimize array placement on a portion of a patient's body, the imaging data 610, such as MRI imaging data, may be analyzed by the patient modeling application 608 to identify a region of interest that comprises a tumor. In the context of a patient's head, to characterize how electric fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model to understand how an externally applied electric field, of preset frequency, will distribute throughout any portion of a patient's body, for example, the brain. The results of these simulations, employing paired array configurations, a constant current, and a preset frequency of 200 kHz, have demonstrated that electric field distributions are relatively non-uniform throughout the brain and that electric field intensities exceeding 1 V/cm are generated in most tissue compartments except CSF. These results are obtained assuming total currents with a peak-to-peak value of 1800 milliamperes (mA) at the transducer array-scalp interface. This threshold of electric field intensity is sufficient to arrest cellular proliferation in glioblastoma cell lines. Additionally, by manipulating the configuration of paired transducer arrays, it is possible to achieve an almost tripling of electric field intensity to a particular region of the brain as shown in FIG. 7. FIG. 7 illustrates electric field magnitude and distribution (in V/cm) shown in the coronal view from a finite element method simulation model. This simulation employs a left-right paired transducer array configuration.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations, and combinations of paired array layouts may be assessed to generate the configuration which delivers maximal electric field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques, or may be performed manually, for example by way of a physician.

Figure 9A:
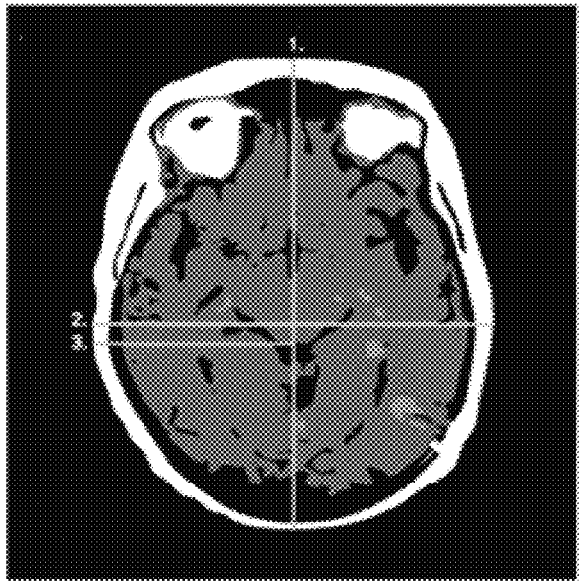
FIG. 9A shows an axial T1 sequence slice containing a most apical image, including orbits used to measure head size.
Figure 9B:
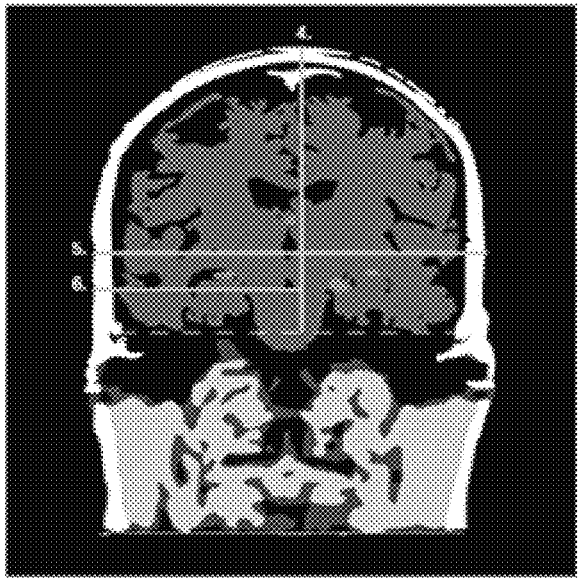
FIG. 9B shows a coronal T1 sequence slice selecting image at the level of ear canal used to measure head size.
Figure 9C:
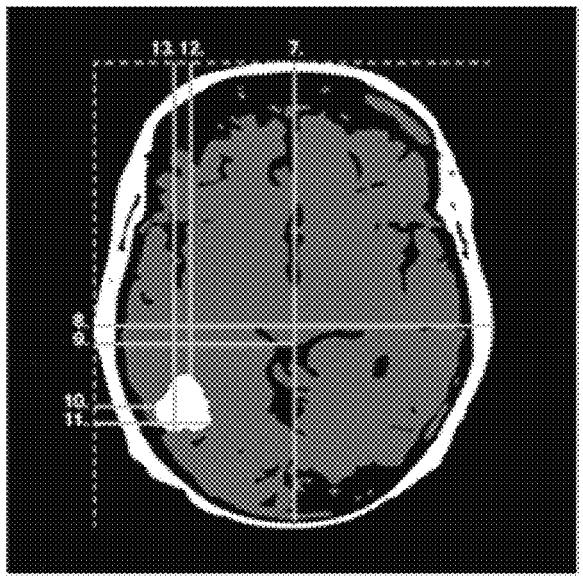
FIG. 9C shows a postcontrast T1 axial image shows maximal enhancing tumor diameter used to measure tumor location.
Figure 9D:
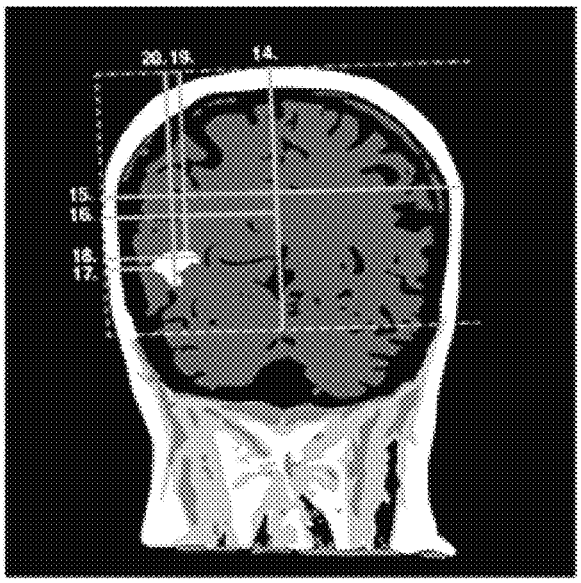
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right frontotemporal tumor, a right parieto-temporal tumor, a left frontotemporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing the most apical image, including orbits used to measure head size. FIG. 9B shows a coronal T1 sequence slice selecting image at the level of ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as: a maximal anteroposterior (A-P) head size, commencing measurement from the outer margin of the scalp; a maximal width of the head perpendicular to the A-P measurement: right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 post-contrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head in to the template space, as well as the inverse transformation that maps the template in to the patient space. The inverse transformation is applied to the 3D deformable template to yield an approximation of the patient head in the absence of a tumor. Finally, the tumor (referred to as a region-of-interest (ROI)) is planted back into the deformed template to yield the full patient model. The patient model may be a digital representation in three dimensional space of the portion of the patient's body, including internal structures, such as tissues, organs, tumors, etc.

TABLE 1

| Tissue Type | Conductivity, S/m | Relative Permittivity |
| --- | --- | --- |
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Delivery of TTFields may then be simulated by the patient modeling application 608 using the patient model. Simulated electric field distributions, dosimetry, and simulation-based analysis are described in U.S. Patent Publication No. 20190117956 A1 and Publication "Correlation of Tumor treating Fields Dosimetry to Survival Outcomes in Newly Diagnosed Glioblastoma: A Large-Scale Numerical Simulation-based Analysis of Data from the Phase 3 EF-14 randomized Trial" by Ballo, et al. (2019) which are incorporated herein by reference in their entirety.

To ensure systematic positioning of the transducer arrays relative to the tumor location, a reference coordinate system may be defined. For example, a transversal plane may initially be defined by conventional LR and AP positioning of the transducer arrays. The left-right direction may be defined as the x-axis, the AP direction may be defined as the y-axis, and the craniocaudal direction normal to the XY-plane may be defined as the Z-axis.

After defining the coordinate system, transducer arrays may be virtually placed on the patient model with their centers and longitudinal axes in the XY-plane. A pair of transducer arrays may be systematically rotated around the z-axis of the head model, e.g., in the XY-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electric field distribution calculations may be performed for each transducer array position relative to tumor coordinates.

Electric field distribution in the patient model may be determined by the patient modeling application 608 using a finite element (FE) approximation of electrical potential. In general, the quantities defining a time-varying electromagnetic field are given by the complex Maxwell equations. However, in biological tissues and at the low to intermediate frequency of TTFields (f=200 kHz), the electromagnetic wavelength is much larger than the size of the head and the electric permittivity $\varepsilon$ is negligible compared to the real-valued electric conductivity $\sigma$, e.g., where $\omega=2\pi f$ is the angular frequency. This implies that the electromagnetic propagation effects and capacitive effects in the tissue are negligible, so the scalar electric potential may be well approximated by the static Laplace equation $\nabla\cdot(\sigma\cdot\phi)=0$, with appropriate boundary conditions at the electrodes and skin. Thus, the complex impedance is treated as resistive (e.g., reactance is negligible) and currents flowing within the volume conductor are, therefore, mainly free (Ohmic) currents. The FE approximation of Laplace's equation was calculated using the SimNIBS software (simnibs.org). Computations were based on the Galerkin method and the residuals for the conjugate gradient solver were required to be <1E-9. Dirichlet boundary conditions were used with the electric potential was set to (arbitrarily chosen) fixed values at each set of electrode arrays. The electric (vector) field was calculated as the numerical gradient of the electric potential and the current density (vector field) was computed from the electric field using Ohm's law. The potential difference of the electric field values and the current densities were linearly rescaled to ensure a total peak-to-peak amplitude for each array pair of 1.8 A, calculated as the (numerical) surface integral of the normal current density components over all triangular surface elements on the active electrode discs. This corresponds to the current level used for clinical TTFields therapy by the Optune® device. The "dose" of TTFields was calculated as the intensity (L2 norm) of the field vectors. The modeled current is assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electric field strength generated by transducer arrays placed at multiple locations on the patient may be determined by the patient modeling application 608 for one or more tissue types. In an aspect, the transducer array position that corresponds to the highest average electric field strength in the tumor tissue type(s) may be selected as a desired (e.g., optimal) transducer array position for the patient. In another aspect, one or more candidate positions for a transducer array(s) may be excluded as a result of a physical condition of the patient. For example, one or more candidate positions may be excluded based on areas of skin irritation, scars, surgical sites, discomfort, etc. Accordingly, the transducer array position that corresponds to the highest average electric field strength in the tumor tissue type(s), after excluding one or more candidate positions, may be selected as a desired (e.g., optimal) transducer array position for the patient. Thus, a transducer array position may be selected that results in less than the maximum possible average electric field strength.

The patient model may be modified to include an indication of the desired transducer array position. The resulting patient model, comprising the indication(s) of the desired transducer array position(s), may be referred to as the three-dimensional array layout map (e.g., three-dimensional array layout map 600). The three-dimensional array layout map may thus comprise a digital representation, in three-dimensional space, of the portion of the patient's body, an indication of tumor location, an indication of a position for placement of one or more transducer arrays, combinations thereof, and the like.

The three-dimensional array layout map may be provided to the patient in a digital form and/or a physical form. The patient, and/or a patient caregiver, may use the three-dimensional array layout map to affix one or more transducer arrays to an associated portion of the patient's body (e.g., head).

Figure 10:
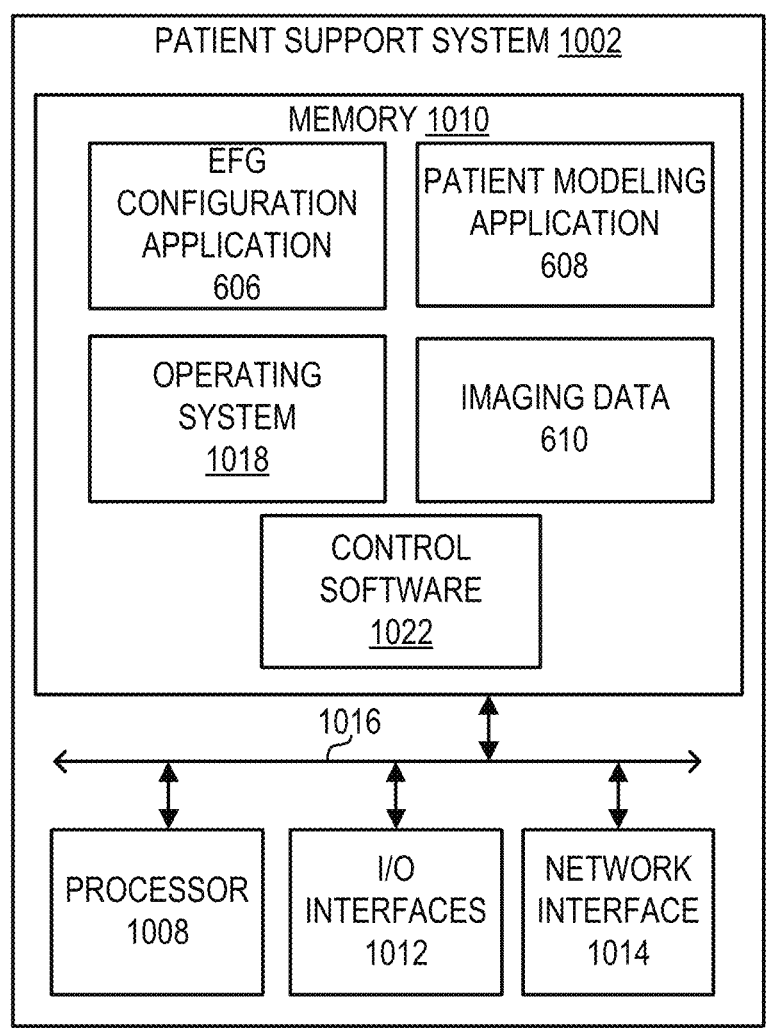
FIG. 10 is a block diagram depicting an example operating environment.

FIG. 10 is a block diagram depicting an environment 1000 comprising a non-limiting example of the patient support system 104. In an aspect, some or all steps of any described method may be performed on a computing device as described herein. The patient support system 104 can comprise one or multiple computers configured to store one or more of the EFG configuration application 606, the patient modeling application 608, the imaging data 610, and the like.

The patient support system 104 can be a digital computer that, in terms of hardware architecture, generally includes a processor 1008, memory system 1010, input/output (I/O) interfaces 1012, and network interfaces 1014. These components (1008, 1010, 1012, and 1014) are communicatively coupled via a local interface 1016. The local interface 1016 can be, for example, but not limited to, one or more buses or other wired or wireless connections, as is known in the art. The local interface 1016 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1008 can be a hardware device for executing software, particularly that stored in memory system 1010. The processor 1008 can be any custom made or commercially available processor, a central processing unit (CPU), an auxiliary processor among several processors associated with the patient support system 1002, a semiconductor-based microprocessor (in the form of a microchip or chipset), or generally any device for executing software instructions. When the patient support system 1002 is in operation, the processor 1008 can be configured to execute software stored within the memory system 1010, to communicate data to and from the memory system 1010, and to generally control operations of the patient support system 1002 pursuant to the software.

The I/O interfaces 1012 can be used to receive user input from and/or for providing system output to one or more devices or components. User input can be provided via, for example, a keyboard and/or a mouse. System output can be provided via a display device and a printer (not shown). I/O interfaces 1012 can include, for example, a serial port, a parallel port, a Small Computer System Interface (SCSI), an IR interface, an RF interface, and/or a universal serial bus (USB) interface.

The network interface 1014 can be used to transmit and receive from the patient support system 1002. The network interface 1014 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1014 may include address, control, and/or data connections to enable appropriate communications.

The memory system 1010 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1010 may incorporate electronic, magnetic, optical, and/or other types of storage media. Note that the memory system 1010 can have a distributed architecture, where various components are situated remote from one another, but can be accessed by the processor 1008.

The software in memory system 1010 may include one or more software programs, each of which comprises an ordered listing of executable instructions for implementing logical functions. In the example of FIG. 10, the software in the memory system 1010 of the patient support system 1002 can comprise the EFG configuration application 606, the patient modeling application 608, the imaging data 610, and a suitable operating system (O/S) 1018. The operating system 1018 essentially controls the execution of other computer programs, and provides scheduling, input-output control, file and data management, memory management, and communication control and related services.

For purposes of illustration, application programs and other executable program components such as the operating system 1018 are illustrated herein as discrete blocks, although it is recognized that such programs and components can reside at various times in different storage components of the patient support system 104. An implementation of the EFG configuration application 606, the patient modeling application 608, the imaging data 610, and/or the control software 110 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In an embodiment, illustrated in FIG. 11, one or more of the apparatus 100, the patient support system 602, the patient modeling application 608, and/any other device/component described herein can be configured to perform a method 1100 comprising, at 1110, causing cyclical application of a first electric field via a first transducer array in a first direction and a second electric field via a second transducer array in a second direction, opposite the first direction, wherein the first transducer array comprises a first plurality of electrodes and the second transducer array comprises a second plurality of electrodes.

In some instances, the first electric field and the second electric field may be applied with a frequency between 50 and 500 kHz and electric field strength of at least 1 V/cm to a tumor.

In some instances, the cyclical application may include applying the first electric field for between 20 and 500 ms in the first direction and the second electric field for between 20 and 500 ms in the second direction during each cycle.

The method 1100 may include, during the cyclical application, at 1120, deactivating, based on a temperature associated with the one or more electrodes of the first plurality of electrodes or one or more electrodes of the second plurality of electrodes satisfying a threshold, the one or more electrodes of the first plurality of electrodes or the one or more electrodes of the second plurality of electrodes, and at 1130, activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes.

In some instances, the method 1100 may include determining that the temperature associated with the one or more electrodes of the first plurality of electrodes or the one or more electrodes of the second plurality of electrodes satisfies the threshold.

In some instances, the method 1100 may include determining that the temperature associated with the deactivated one or more electrodes of the first plurality of electrodes or the deactivated one or more electrodes of the second plurality of electrodes no longer satisfies the threshold.

In some instances, the method 1100 may include, during the cyclical application, selectively deactivating, one or more electrodes of the first plurality of electrodes or one or more electrodes of the second plurality of electrodes, to adjust an angle at which the first electric field or the second electric field is applied to the region of interest. In some instances, selectively deactivating the one or more electrodes of the first plurality of electrodes or the one or more electrodes of the second plurality of electrodes may be based on a random selection of angles at an optimal duty cycle. In some instances, selectively deactivating the one or more electrodes of the first plurality of electrodes or the one or more electrodes of the second plurality of electrodes may be based on a random selection of angles at a temperature-limited duty cycle. In some instances, selectively deactivating the one or more electrodes of the first plurality of electrodes or the one or more electrodes of the second plurality of electrodes may be based on the selection of angles that are orthogonal relative to a geometric center of the region of interest. In some instances, selectively deactivating the one or more electrodes of the first plurality of electrodes or the one or more electrodes of the second plurality of electrodes may be based on the selection of angles that are orthogonal relative to pairs of cathode electrodes and anode electrodes that are orthogonal to each other. In some instances, selectively deactivating the one or more electrodes of the first plurality of electrodes or the one or more electrodes of the second plurality of electrodes may be based on the selection of angles that are most distant from previous angles used within a current duty cycle.

In an embodiment, illustrated in FIG. 12, one or more of the apparatus 100, the patient support system 602, the patient modeling application 608, and/any other device/component described herein can be configured to perform a method 1200 comprising, at 1210, causing cyclical application of a first electric field via a first transducer array in a first direction and a second electric field via a second transducer array in a second direction, opposite the first direction, to a region of interest, wherein the first transducer array comprises a first plurality of electrodes and the second transducer array comprises a second plurality of electrodes.

At 1220, during the cyclical application, selectively deactivating, one or more electrodes of the first plurality of electrodes or one or more electrodes of the second plurality of electrodes, to adjust an angle at which the first electric field or the second electric field is applied to the region of interest. In some instances, selectively deactivating the one or more electrodes of the first plurality of electrodes or the one or more electrodes of the second plurality of electrodes may be based on a random selection of angles at an optimal duty cycle. In some instances, selectively deactivating the one or more electrodes of the first plurality of electrodes or the one or more electrodes of the second plurality of electrodes may be based on a random selection of angles at a temperature-limited duty cycle.

In some instances, selectively deactivating the one or more electrodes of the first plurality of electrodes or the one or more electrodes of the second plurality of electrodes may be based on the selection of angles that are orthogonal relative to a geometric center of the region of interest.

In some instances, selectively deactivating the one or more electrodes of the first plurality of electrodes or the one or more electrodes of the second plurality of electrodes may be based on the selection of angles that are orthogonal relative to pairs of cathode electrodes and anode electrodes that are orthogonal to each other.

In some instances, selectively deactivating the one or more electrodes of the first plurality of electrodes or the one or more electrodes of the second plurality of electrodes may be based on the selection of angles that are most distant from previous angles used within a current duty cycle.

The method 1200 may include, during the cyclical application, deactivating, based on a temperature associated with the one or more electrodes of the first plurality of electrodes or the one or more electrodes of the second plurality of electrodes satisfying a threshold, the one or more electrodes of the first plurality of electrodes or the one or more electrodes of the second plurality of electrodes, and activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes.

In some instances, selectively deactivating the one or more electrodes of the first plurality of electrodes or the one or more electrodes of the second plurality of electrodes may be based on a random selection of angles at an optimal duty cycle and a temperature associated deactivation state of one or more electrodes.

In some instances, selectively deactivating the one or more electrodes of the first plurality of electrodes or the one or more electrodes of the second plurality of electrodes may be based on a random selection of angles at a temperature-limited duty cycle and a temperature associated deactivation state of one or more electrodes.

In some instances, selectively deactivating the one or more electrodes of the first plurality of electrodes or the one or more electrodes of the second plurality of electrodes may be based on the selection of angles that are orthogonal relative to a geometric center of the region of interest and a temperature associated deactivation state of one or more electrodes.

In some instances, selectively deactivating the one or more electrodes of the first plurality of electrodes or the one or more electrodes of the second plurality of electrodes may be based on the selection of angles that are orthogonal relative to pairs of cathode electrodes and anode electrodes that are orthogonal to each other and a temperature associated deactivation state of one or more electrodes.

In some instances, selectively deactivating the one or more electrodes of the first plurality of electrodes or the one or more electrodes of the second plurality of electrodes may be based on the selection of angles that are most distant from previous angles used within a current duty cycle.

In some instances, selectively deactivating the one or more electrodes of the first plurality of electrodes or the one or more electrodes of the second plurality of electrodes may be based on a weighted product of temperature multiplied by a function of the angle between the temperature difference.

In view of the described apparatuses, systems, and methods and variations thereof, hereinbelow are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: causing cyclical application of a first electric field via a first transducer array in a first direction and a second electric field via a second transducer array in a second direction, opposite the first direction, wherein the first transducer array comprises a first plurality of electrodes and the second transducer array comprises a second plurality of electrodes, and during the cyclical application, deactivating, based on a temperature associated with the one or more electrodes of the first plurality of electrodes or one or more electrodes of the second plurality of electrodes satisfying a threshold, the one or more electrodes of the first plurality of electrodes or the one or more electrodes of the second plurality of electrodes, activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes.

Embodiment 2: The embodiment as in any one of the preceding embodiments wherein the first electric field and the second electric field are applied with a frequency between 50 and 500 kHz and an electric field strength of at least 1 V/cm to a tumor.

Embodiment 3: The embodiment as in any one of the preceding embodiments, wherein cyclical application comprises applying the first electric field applied for between 20 and 500 ms in the first direction and the second electric field for between 20 and 500 ms in the second direction during each cycle.

Embodiment 4: The embodiment as in any one of the preceding embodiments further comprising determining that the temperature associated with the one or more electrodes of the first plurality of electrodes or the one or more electrodes of the second plurality of electrodes satisfies the threshold.

Embodiment 5: The embodiment as in any one of the preceding embodiments further comprising determining that the temperature associated with the deactivated one or more electrodes of the first plurality of electrodes or the deactivated one or more electrodes of the second plurality of electrodes no longer satisfies the threshold.

Embodiment 6: The embodiment as in any one of the preceding embodiments further comprising during the cyclical application, selectively deactivating, one or more electrodes of the first plurality of electrodes or one or more electrodes of the second plurality of electrodes, to adjust an angle at which the first electric field or the second electric field is applied to the region of interest.

Embodiment 7: The embodiment as in any one of the preceding embodiments, wherein selectively deactivating is based on a random selection of angles at an optimal duty cycle.

Embodiment 8: The embodiment as in any one of the embodiments 1-6, wherein selectively deactivating is based on a random selection of angles at a temperature-limited duty cycle.

Embodiment 9: The embodiment as in any one of the embodiments 1-6, wherein selectively deactivating is based on selection of angles that are one or more of: most distant from previous angles used within a current duty cycle, and orthogonal relative to a geometric center of the region of interest.

Embodiment 10: The embodiment as in any one of the embodiments 1-6, wherein selectively deactivating is based on selection of angles that are one or more of: most distant from previous angles used within a current duty cycle, and orthogonal relative to pairs of cathode electrodes and anode electrodes that are orthogonal to each other.

Embodiment 11: A method comprising: causing cyclical application of a first electric field via a first transducer array in a first direction and a second electric field via a second transducer array in a second direction, opposite the first direction, to a region of interest, wherein the first transducer array comprises a first plurality of electrodes and the second transducer array comprises a second plurality of electrodes, and during the cyclical application, selectively deactivating, one or more electrodes of the first plurality of electrodes or one or more electrodes of the second plurality of electrodes, to adjust an angle at which the first electric field or the second electric field is applied to the region of interest.

Embodiment 12: The embodiment as in the embodiment 11, wherein selectively deactivating is based on a random selection of angles at an optimal duty cycle.

Embodiment 13: The embodiment as in the embodiment 11, wherein selectively deactivating is based on a random selection of angles at a temperature-limited duty cycle.

Embodiment 14: The embodiment as in the embodiment 11, wherein selectively deactivating is based on selection of angles that are one or more of: most distant from previous angles used within a current duty cycle, and orthogonal relative to a geometric center of the region of interest.

Embodiment 15: The embodiment as in the embodiment 11, wherein selectively deactivating is based on selection of angles that are one or more of: most distant from previous angles used within a current duty cycle, and orthogonal relative to pairs of cathode electrodes and anode electrodes that are orthogonal to each other.

Embodiment 16: The embodiment as in the embodiment 11, wherein during the cyclical application, the method further comprises: deactivating, based on a temperature associated with the one or more electrodes of the first plurality of electrodes or the one or more electrodes of the second plurality of electrodes satisfying a threshold, the one or more electrodes of the first plurality of electrodes or the one or more electrodes of the second plurality of electrodes, and activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes.

Embodiment 17: The embodiment as in the embodiment 16, wherein selectively deactivating is based on a random selection of angles at an optimal duty cycle and a temperature associated deactivation state of one or more electrodes.

Embodiment 18: The embodiment as in the embodiment 16, wherein selectively deactivating is based on a random selection of angles at a temperature-limited duty cycle and a temperature associated deactivation state of one or more electrodes.

Embodiment 19: The embodiment as in the embodiment 16, wherein selectively deactivating is based on selection of angles that are one or more of: most distant from previous angles used within a current duty cycle, and orthogonal relative to a geometric center of the region of interest and a temperature associated deactivation state of one or more electrodes.

Embodiment 20: The embodiment as in the embodiment 16, wherein selectively deactivating is based on selection of angles that are one or more of: most distant from previous angles used within a current duty cycle, and orthogonal relative to pairs of cathode electrodes and anode electrodes that are orthogonal to each other and a temperature associated deactivation state of one or more electrodes.

Embodiment 21: The embodiment as in the embodiment 16, wherein selectively deactivating is based on a weighted product of temperature multiplied by a function of the angle between the difference in temperature.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
    causing cyclical application of a first electric field via a first transducer array in a first direction and a second electric field via a second transducer array in a second direction, opposite the first direction, wherein the first transducer array comprises a first plurality of electrodes disposed on a first substrate and the second transducer array comprises a second plurality of electrodes disposed on a second substrate; and
    during the cyclical application,
    deactivating, based on a temperature associated with one or more electrodes of the first plurality of electrodes or one or more electrodes of the second plurality of electrodes satisfying a threshold, the one or more electrodes of the first plurality of electrodes or the one or more electrodes of the second plurality of electrodes,
    activating, based on a temperature associated with the deactivated one or more electrodes of the first plurality of electrodes or the deactivated one or more electrodes of the second plurality of electrodes no longer satisfying the threshold, the deactivated one or more electrodes of the first plurality of electrodes or the deactivated one or more electrodes of the second plurality of electrodes;
    determining a selection of angles, wherein determining the selection of angles comprises at least one of:
        determining a duty cycle for the cyclical application and determining a random selection of angles at the duty cycle; or
        determining a temperature-limited duty cycle for the cyclical application and determining a random selection of angles at the temperature-limited duty cycle; and
    during the cyclical application, selectively deactivating, based on the selection of angles at the duty cycle or at the temperature-limited duty cycle, the one or more electrodes of the first plurality of electrodes or the one or more electrodes of the second plurality of electrodes, to adjust an angle at which the first electric field or the second electric field is applied to a region of interest, wherein the angle is adjusted to one of the random selection of angels.

2. The method of claim 1, wherein the first electric field and the second electric field are applied with a frequency between 50 and 500 kHz and an electric field strength of at least 1 V/cm to a tumor.

3. The method of claim 1, wherein the cyclical application comprises applying the first electric field for between 20 and 500 ms in the first direction and the second electric field for between 20 and 500 ms in the second direction during each cycle.

4. The method of claim 1, further comprising determining that the temperature associated with the one or more electrodes of the first plurality of electrodes or the one or more electrodes of the second plurality of electrodes satisfies the threshold.

5. The method of claim 1, further comprising determining that the temperature associated with the deactivated one or more electrodes of the first plurality of electrodes or the deactivated one or more electrodes of the second plurality of electrodes no longer satisfies the threshold.

6. The method of claim 1, wherein determining the selection of angles comprises determining a selection of angles that are one or more of: most distant from previous angles used within a current duty cycle, or orthogonal relative to a geometric center of the region of interest.

7. The method of claim 1, wherein determining the selection of angles comprises:
   determining a selection of angles that are one or more of: most distant from previous angles used within a current duty cycle, or orthogonal relative to pairs of cathode electrodes and anode electrodes that are orthogonal to each other.

8. The method of claim 1, wherein deactivating the one or more electrodes of the first plurality of electrodes or the one or more electrodes of the second plurality of electrodes comprises deactivating one or more but less than all of the electrodes of the first plurality of electrodes or one or more but less than all of the electrodes of the second plurality of electrodes.

9. The method of claim 1, comprising a method of applying tumor treating fields to a subject's body.

\* \* \* \* \*